(12) United States Patent
Lin et al.

(10) Patent No.: US 9,181,581 B2
(45) Date of Patent: Nov. 10, 2015

(54) AUTOMATIC GENECHIP ARRAY DIAGNOSING APPARATUS

(71) Applicant: Fooyin University Hospital, Pingtung County (TW)

(72) Inventors: Shiu-Ru Lin, Kaohsiung (TW); Hui-Jen Chang, Kaohsiung County (TW); Suz-Kai Hsiung, Kaohsiung County (TW); Chan-Han Wu, Pingtung County (TW)

(73) Assignee: FOOYIN UNIVERSITY HOSPITAL, Pingtung County (TW)

( * ) Notice: Subject to any disclaimer, the term of this patent is extended or adjusted under 35 U.S.C. 154(b) by 0 days.

(21) Appl. No.: 14/225,949

(22) Filed: Mar. 26, 2014

(65) Prior Publication Data

US 2014/0206571 A1    Jul. 24, 2014

Related U.S. Application Data

(63) Continuation of application No. 12/849,264, filed on Aug. 3, 2010, now abandoned.

(30) Foreign Application Priority Data

May 13, 2010    (TW) .................................. 099115356

(51) Int. Cl.
*G01N 35/00* (2006.01)
*G01N 35/10* (2006.01)
*C12Q 1/68* (2006.01)
*G01N 33/533* (2006.01)
*C40B 20/02* (2006.01)

(52) U.S. Cl.
CPC .......... *C12Q 1/6837* (2013.01); *G01N 35/0098* (2013.01); *G01N 35/0099* (2013.01); *G01N 2035/00158* (2013.01); *G01N 2035/00326* (2013.01); *G01N 2035/00356* (2013.01); *G01N 2035/00524* (2013.01); *G01N 2035/00564* (2013.01)

(58) Field of Classification Search
CPC .......... G01N 2035/00158; G01N 2035/00326; G01N 35/0099; G01N 35/0098; G01N 2035/00346–2035/00425; G01N 2035/00524; G01N 2035/00564–2035/00574
See application file for complete search history.

(56) References Cited

U.S. PATENT DOCUMENTS

| 2005/0084867 | A1* | 4/2005 | Caren et al. ................. 435/6 |
| 2006/0110296 | A1* | 5/2006 | Tajima et al. ............... 422/101 |
| 2006/0147957 | A1* | 7/2006 | Qian et al. ................... 435/6 |

* cited by examiner

*Primary Examiner* — Jeremy C Flinders
(74) *Attorney, Agent, or Firm* — Jackson IPG PLLC; Demian K. Jackson

(57) ABSTRACT

A method of diagnosing a sample with an automated genechip array for a fast diagnosis having high accuracy, where the sample is processed through lysis, separation, purification, labeling, reacting in the genechip array, taking a photo thereafter and analyzing the photo.

6 Claims, 3 Drawing Sheets

AUTOMATIC GENECHIP ARRAY DIAGNOSING APPARATUS

RELATED APPLICATIONS

This application is a continuation of U.S. Ser. No. 12/849,264 filed Aug. 3, 2010 and entitled "Automatic Genechip Array Diagnosing Apparatus".

TECHNICAL FIELD OF THE DISCLOSURE

The present disclosure relates to diagnosis using a genechip array; more particularly, relates to methods of processing a sample by an automatic apparatus to be reacted in a genechip array for a fast diagnosis having high accuracy.

DESCRIPTION OF THE RELATED ARTS

In a general molecular diagnosis, pretreatment and purification procedures to a sample for biological clinics are critical. Yet, traditionally, basic experimental technologies take too much time, like pretreatment of the sample; not to mention that it is hard to extract and purify deoxyribonucleic acid (DNA) and ribonucleic acid (RNA) of the sample. Moreover, some complex manual operations and steps increase waste of the sample and decrease accuracy of the diagnosis. Hence, the prior arts do not fulfill all users' requests on actual use.

SUMMARY OF THE INVENTION

The main purpose of the present disclosure is to process a sample by an automatic apparatus for a fast diagnosis having high accuracy, where the sample is processed through lysis, separation, purification, labeling, reacting in a genechip array, taking a photo thereafter and analyzing the photo.

To achieve the above purpose, the present disclosure includes an automatic genechip array diagnosing apparatus, comprising a loading tray, an active mixing device, a temperature controlling device, a reagent storing device, a fluid manipulation device, a magnetic controlling device, an image acquiring device and an operating device, where the loading tray has a sample pretreatment area, a sample purification area, a transcription and probe labeling area and a genechip reaction and imaging area on a surface of the loading tray; where the loading tray is an operation platform to load a sample and a genechip array; where the active mixing device is connected with the loading tray; where the active mixing device shakes the loading tray to mix the sample, a reagent and the genechip array in the loading tray; where the temperature controlling device is connected with the loading tray to control temperature in the loading tray; where the reagent storing device comprises a plurality of reagent vessels and a magnetic beads storing area; where the reagent storing device provides the reagent to the sample; where the fluid manipulation device is set between the loading tray and the reagent storing device; where the fluid manipulation device provides the reagent to the loading tray; where the fluid manipulation device transfers the sample between areas of the loading tray; where the fluid manipulation device discharges a waste liquid obtained after the reaction of the sample; where the magnetic controlling device is connected with the loading tray; where the magnetic controlling device purifies the sample with coordination of a plurality of magnetic beads in the magnetic beads storing area; where the image acquiring device is corresponding to the genechip reaction and imaging area to obtain photos of the sample and the genechip array after the reaction and a development process; and where the operating device is connected with the loading tray, the active mixing device, the temperature controlling device, the reagent storing device, the fluid manipulation device, the magnetic controlling devices and the image acquiring device to control operation, analyze photo and show data. Accordingly, a novel automatic genechip array diagnosing method is obtained.

BRIEF DESCRIPTIONS OF THE DRAWINGS

The present disclosure will be better understood from the following detailed description of the preferred embodiment according to the present disclosure, taken in conjunction with the accompanying drawings, in which FIG. 1 is the structural view showing the preferred embodiment according to the present disclosure;

DESCRIPTION OF THE PREFERRED EMBODIMENT

The following description of the preferred embodiment is provided to understand the features and the structures of the present disclosure.

Figure 1:
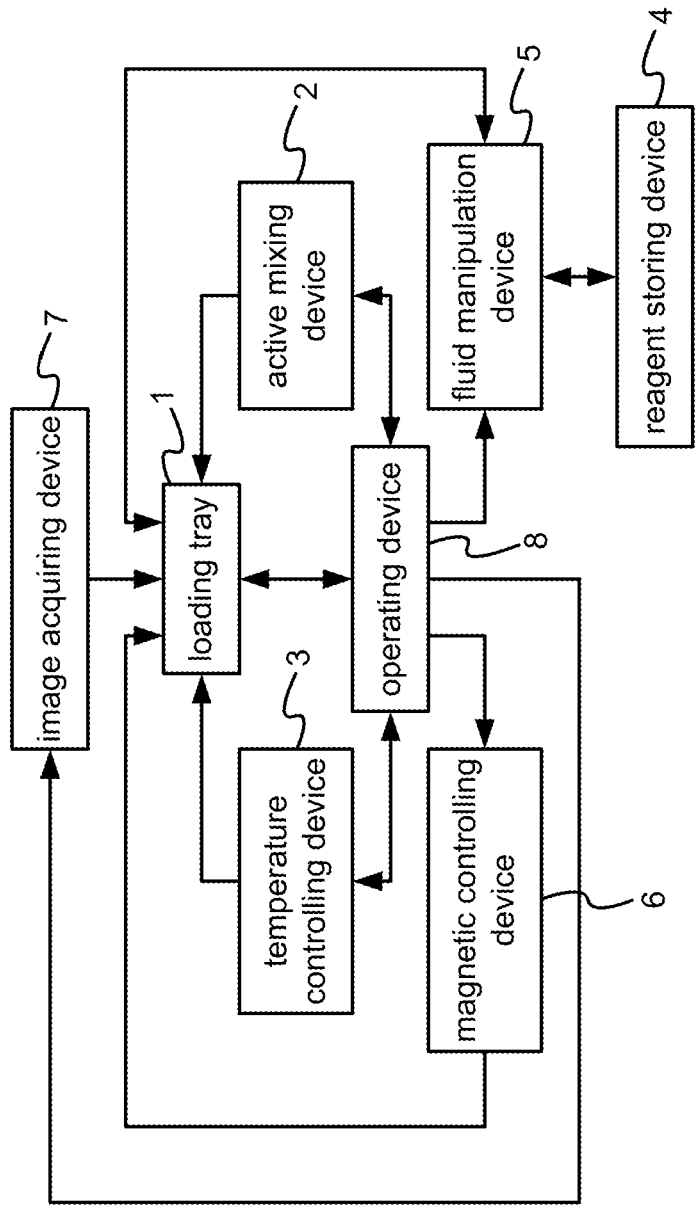
Figure 2:
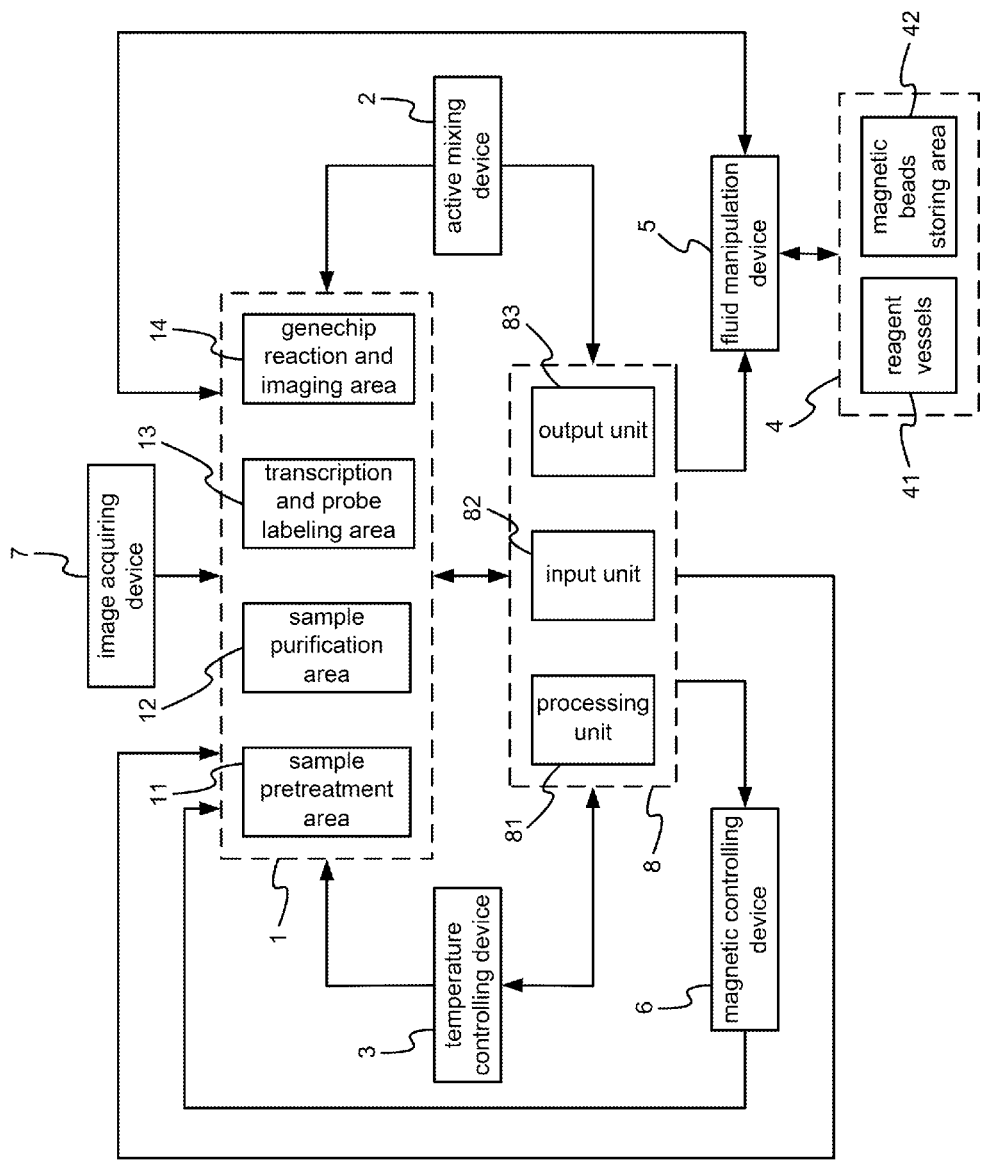
FIG. 2 is the block view showing the preferred embodiment.
Figure 3:
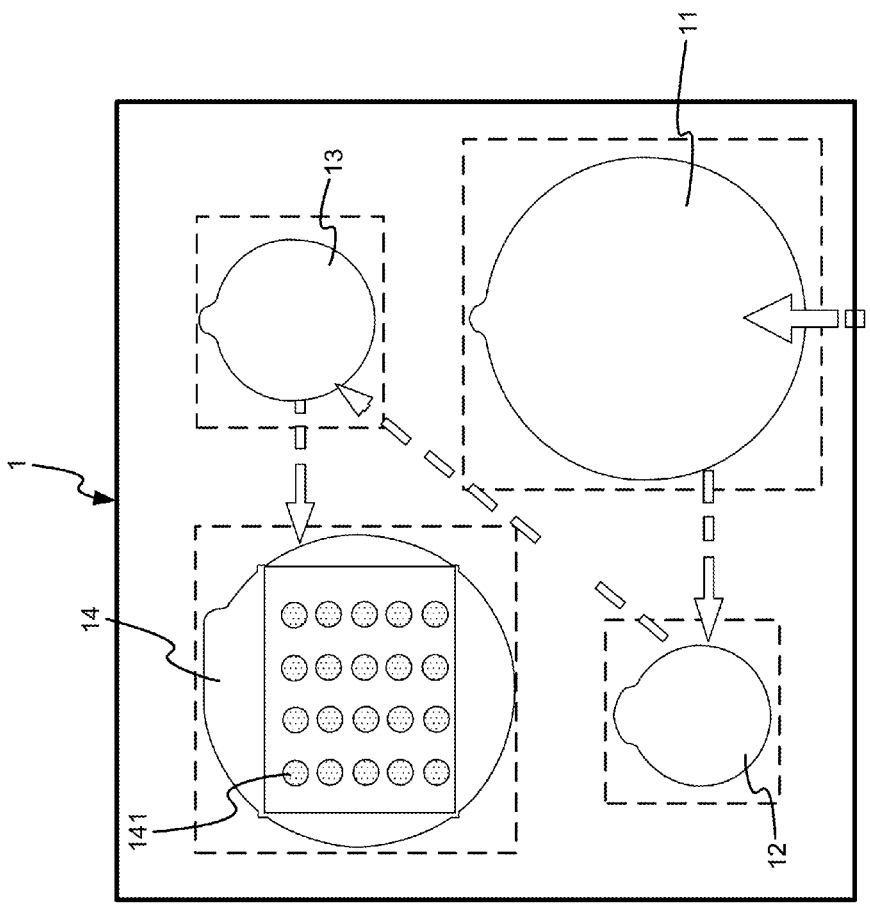
FIG. 3 is the view showing the loading tray.

Please refer to FIG. 1 to FIG. 3, which are a structural view and a block view showing a preferred embodiment according to the present disclosure; and a view showing a loading tray. As shown in the figures, the present disclosure includes an automatic genechip array diagnosing apparatus, comprising a loading tray 1, an active mixing device 2, a temperature controlling device 3, a reagent storing device 4, a fluid manipulation device 5, a magnetic controlling device 6, an image acquiring device 7 and an operating device 8.

On a surface of the loading tray 1, the loading tray 1 has a sample pretreatment area 11, a sample purification area 12, a transcription and probe labeling area 13 and a genechip reaction and imaging area 14, where the loading tray 1 is used as an operation platform for loading a sample and a genechip array on processing a diagnosis. The genechip reaction and imaging area 14 is set with a genechip array 141; and each genechip in the genechip array 141 has a plurality of probes. A chemical enzyme colorimetric development method is processed after a reaction between the sample and the probes in the genechip array 141.

The active mixing device 2 is connected with the loading tray 1, which shakes the loading tray 1 on processing the diagnosis. The active mixing device 2 is a servo motor.

The temperature controlling device 3 is connected with the loading tray 1, which controls temperature of the loading tray 1 on processing the diagnosis.

The reagent storing device 4 comprises a plurality of reagent vessels 41 and a magnetic beads storing area 42, which provides a reagent for the sample on processing the diagnosis.

The fluid manipulation device 5 is set between the loading tray 1 and the reagent storing device 4, which provides the reagent to the loading tray 1, transfers the sample between areas of the loading tray 1 and discharges a waste liquid generated after the reaction of the sample. The fluid manipulation device 5 is a vacuum suction device.

The magnetic controlling device 6 is connected with the loading tray 1, which purifies the sample with coordination of a plurality of magnetic beads in the magnetic beads storing area 42.

The image acquiring device 7 is corresponding to the genechip reaction and imaging area 14, which takes photos of the sample and the genechip array after the reaction and a development process. The image acquiring device 7 is a photosensitive device.

The operating device 8 is connected with the loading tray 1, the active mixing device 2, the temperature controlling device 3, the reagent storing device 4, the fluid manipulation device 5, the magnetic controlling device 6 and the image acquiring device 7 to control operation, analyze photo and show data. The operating device 8 comprises a processing unit 81; an input unit 82 connected with the processing unit 81; and an output unit 83 connected with the processing unit 81, where the processing unit 81 is a programmable logical array; where the input unit 82 comprises a plurality of pressing bottoms; and where the output unit 83 is a display.

Thus, a novel automatic genechip array diagnosing apparatus is obtained.

On using the present disclosure, a method is processed with the following steps:

(a) A sample (e.g. blood) is transferred to the sample pretreatment area 11 of the loading tray 1 injected with a lysis processing solution. The sample pretreatment area 11 is then heated to a temperature of 35~80° C. by the temperature controlling device; and, the magnetic beads and a reagent for separation and purification in the magnetic beads storing area 42 of the reagent storing device are transferred to the sample pretreatment area 11 by the fluid manipulation device 5. Then, the active mixing device 2 shakes the loading tray 1 at a speed of 100~200 rpm to mix the sample, the magnetic beads and the reagent for effectively jointing the magnetic beads with the sample.

(b) The sample jointed with the magnetic beads in the sample pretreatment area 11 is transferred to the sample purification area 12 by the fluid manipulation device 5. Then the sample is purified by attracting the magnetic beads with the magnetic controlling device 6. A supernatant without the magnetic beads in the sample purification area 12 are then removed by the fluid manipulation device 5.

(c) A reaction solution obtained from the reagent vessels 41 by the fluid manipulation device 5 is added into the sample purification area 12; and, the magnetic controlling device 6 is shut down to make the magnetic beads float. The active mixing device 2 then shakes the loading tray 1 at a speed of 100~200 rpm to fully mix the magnetic beads with the reaction solution. Thus, after the sample and the magnetic beads are separated, molecules are released.

(d) A solution containing the molecules in the sample purification area 12 is transferred to the transcription and probe labeling area 13 by the fluid manipulation device 5. The reaction solution in the reagent vessels 41 is sucked into the transcription and probe labeling area 13 by the fluid manipulation device 5. The active mixing device 2 shakes the loading tray 1 at a speed of 100~200 rpm; and, the transcription and probe labeling area 13 is heated to a temperature of 35~80° C. by the temperature controlling device 3. Thus, a reaction of transcription and labeling to the sample is accomplished.

(e) After the transcription and labeling in the transcription and probe labeling area 13 is accomplished, the molecules of the sample are transferred to the genechip reaction and imaging area 14 by the fluid manipulation device 5 for reaction. A plurality of reaction solutions in the reagent vessels 41 is sucked by the fluid manipulation device 4 to be placed into the genechip reaction and imaging area 14. Then, the active mixing device 2 shakes the loading tray 1 at a speed of 100~200 rpm; and, the genechip reaction and imaging area 14 is heated to a temperature of 35~80° C. by the temperature controlling device 3. Thus, a specific bonding is done by probes in the genechip array 141 for development with a reagent.

(f) A developed photo is obtained from the genechip reaction and imaging area 14 through the image acquiring device 7 after the bonding reaction of the molecules and the probes in the genechip array 141. The photo is then discriminated, transferred or showed through the input unit 81 and the output unit 82 of the operating device 8 with coordination of the processing unit 83. The photo taken by the image acquiring device 7 is thus analyzed to finish diagnosing the specific molecules in the sample.

Thus, the present disclosure operates an automatic diagnosis through the above steps with coordination of devices disclosed in the present disclosure for reducing manual error, accelerating reaction speed, and shortening diagnosis time.

To sum up, the present disclosure includes an automatic genechip array diagnosing apparatus and method, where a sample is diagnosed with automatic devices for a fast diagnosis having high accuracy.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. An automatic genechip array diagnosing method, comprising:

transferring a sample to a sample pretreatment area designated in a first corner of a rectangular loading tray injected with a processing solution;

heating the sample pretreatment area;

transferring magnetic beads and a reagent for separation and purification from a magnetic beads storing area and from a reagent storing device respectively to the sample pretreatment area with a fluid manipulation device;

shaking the loading tray so as to mix the sample, the magnetic beads and the reagent to join the magnetic beads with the sample;

transferring the sample joined with the magnetic beads in the sample pretreatment area to a sample purification area designated in a second corner of the loading tray with the fluid manipulation device;

purifying the sample by attracting the magnetic beads with a magnetic controlling device;

removing a supernatant without the magnetic beads in the sample purification area with the fluid manipulation device;

adding reaction solution into the sample purification area with the fluid manipulation device and then shaking the loading tray to fully mix the magnetic beads with the reaction solution such that molecules are released after the sample and the magnetic beads are separated;

transferring a solution containing the molecules in the sample purification area to a transcription and probe labeling area designated in a third corner of the loading tray with the fluid manipulation device;

sucking a reaction solution into the transcription and probe labeling area with the fluid manipulation device;

shaking the loading tray and heating the transcription and probe labeling area such that a reaction of transcription and labeling to the sample occurs;

then transferring the molecules of the sample to a genechip reaction and imaging area designated in a fourth corner of the loading tray with the fluid manipulation device;

sucking a plurality of reaction solutions into the genechip reaction and imaging area with the fluid manipulation device;

then shaking the loading tray and heating the genechip reaction and imaging area such that a specific bonding is done by a plurality of probes in the genechip array for development with a reagent;

obtaining a developed photo from the genechip reaction and imaging area after the bonding reaction of the molecules and the probes in the genechip array; and then discriminating, transferring or showing the photo taken to finish diagnosing the specific molecules in the sample.

2. The method of claim 1, wherein transferring the sample comprises transferring blood.

3. The method of claim 1, wherein the processing solution is a lysis processing solution.

4. The method of claim 1, wherein heating comprises heating to a temperature of 35-80° C.

5. The method of claim 1, shaking the loading tray is performed at a speed of 100-200 rpm.

6. The method of claim 1, wherein the step of adding reaction solution into the sample purification area and then shaking the loading tray to fully mix the magnetic beads with the reaction solution further comprises shutting down the magnetic controlling device to allow the magnetic beads to float.

* * * * *